(12) United States Patent
Casati et al.

(10) Patent No.: US 6,765,662 B2
(45) Date of Patent: Jul. 20, 2004

(54) SURFACE ANALYSIS

(75) Inventors: Donato Casati, Merate (IT); Fabio Mauri, Milan (IT)

(73) Assignee: International Business Machines Corporation, Armonk, NY (US)

( * ) Notice: Subject to any disclaimer, the term of this patent is extended or adjusted under 35 U.S.C. 154(b) by 584 days.

(21) Appl. No.: 09/859,171

(22) Filed: May 16, 2001

(65) Prior Publication Data

US 2002/0001077 A1 Jan. 3, 2002

(30) Foreign Application Priority Data

May 22, 2000 (GB) .............................................. 0012184

(51) Int. Cl.$^7$ ........................... G01B 1/00; G01N 13/00
(52) U.S. Cl. ..................... 356/150; 73/64.52; 73/150 A
(58) Field of Search ........................ 356/150; 73/150 A, 73/64.52

(56) References Cited

U.S. PATENT DOCUMENTS

| | | | | |
|---|---|---|---|---|
| 4,910,402 A | * | 3/1990 | McMillan | 250/341.2 |
| 5,137,352 A | * | 8/1992 | Blitshteyn et al. | 356/138 |
| 5,268,733 A | | 12/1993 | Wright et al. | 356/150 |
| 5,559,339 A | * | 9/1996 | Domanik et al. | 250/573 |

* cited by examiner

*Primary Examiner*—Tu Nguyen
*Assistant Examiner*—Roy M. Punnoose
(74) *Attorney, Agent, or Firm*—William H. Steinberg

(57) ABSTRACT

A method and apparatus for estimating the adhesion properties of a surface of an article by holding the article so that the surface is facing downwards and placing a droplet of liquid against the surface. The volume of the droplet is incremented until the droplet reaches a critical weight at which some of the liquid drops for the action of the gravity force. The higher is the critical weight, the stronger the mutual adhesion forces between the liquid and the surface. If the characteristics of the liquid are kept constant, it is possible to obtain an immediate evaluation of the adhesiveness of a surface by comparing the measured critical weight with experimental results.

13 Claims, 1 Drawing Sheet

SURFACE ANALYSIS

FIELD OF INVENTION

The present invention relates to a method and apparatus for analyzing the characteristics of a surface and more particularly for determining the adhering properties of a solid surface.

BACKGROUND OF THE INVENTION

Understanding what happens on surfaces when materials interact one each other is fundamental in many industrial processes. Many assembly operations in microelectronics manufacturing need a precise assessment of the adhering properties of a surface, particularly in all those cases which involve the joining of two surfaces or the coating of a surface. For example metal surfaces might need to be cleaned and etched before being used in processes like soldering, electroplating, bonding or painting. A check of surface characteristics may also be required for silicon semiconductors before covering with protective resins. Another example of an operation needing an assessment of adhesion is the bonding of heat-sink to a device in order to predict the reliability of the joining.

Another example is represented by manufacturing processes requiring plastic parts to be painted or coated, not only for decorative purposes, but also for a number of functional reasons, e.g. for improving mechanical and chemical resistance (i.e. anti-scratch and anti-reflection coating for CR-39 optical lens), ESD and/or MFI shielding (polymer medullization).

Very often, plastic surfaces have a poor tendency to bond to other materials and offer low adhesion characteristics, making the painting process of the surface very difficult, because of the bad interaction of the plastic surface with the coating layer. The main reason for the low adhesion of plastic surfaces is the inherent inert chemical structure of polymers, which gives a low surface energy, and the presence of additives in their chemical composition, such as plasticizers, antioxidants and antistatics.

For the above reasons, a precise assessment of the adhering properties of a surface before its use is very important.

These properties are generally related to the chemical nature of the surface, but in the case of inorganic surface they are strictly dependent on the surface cleanliness. Many circumstances require that the cleanliness of a surface is tested and measured to verify that the contamination of the part is contained within acceptable limits. Furthermore, a check on the cleanliness of a surface may be required when a part is moved between two following steps and handling or transportation is required. For example a cleaning or a check of the degree of cleanliness may be required before electroplating of a part, or before a component is soldered onto a plated pad. An example is the mounting of a chip (device) on a substrate, usually done through soldering: this is called "first level packaging". This stage of the process needs to be performed in a "clean" environment to avoid contamination of the parts, before the module is encapsulated, usually with a resin, and the circuits are protected by external agents.

In the manufacturing of electronic components and products, the contamination of a surface can be caused by a number of different factors. Examples of causes of contamination are particulates, i.e. through the deposition of small particles; ionic contamination; deposition of chemical compound layers (e.g. oils or salts) occurring during the manufacturing steps; adsorption of organic material (e.g. hydrocarbons or moisture) caused by the exposition to the atmosphere.

If a degree of surface adhesion must be ensured, a reliable method of measurement of such degree has to be fixed.

One of the state of the art methods used to measure the adhering properties of a surface is the so called "contact angle" method. The contact angle method is based on the measurement of the surface wettability. The contact angle is the angle between the substrate surface and the tangent of a liquid droplet deposited on the substrate at the point of contact of the liquid droplet with the substrate surface. This contact angle depends on the surface wettability. An ideal perfect wettability would cause the droplet to spread out over the substrate, giving a contact angle next to 0 degrees. A good wettability value would indicate a clean surface, while a bad wettability is symptom of organic contamination of the surface. By detecting any displacement on the wettability value from the expected one, an accurate estimate of the cleanliness degree can be derived.

It is known to measure this contact angle by projecting a profile image of the deposited droplet on a screen and estimating the contact angle by measurement on the projected image. One problem with this method is that the measurement of the angle is subject to significant errors and it is unreliable because of human intervention.

U.S. Pat. No. 5,268,733 describes a method for determining the contact angle by measuring, on a projected image of the droplet, the angle between a base line defined by the substrate surface and a reference line, which connects the contact point of the droplet with the substrate and an apex point of the droplet. This method provides a more reliable measurement of the contact angle, but still suffers of the difficulty of the measurement and of the human intervention in the determination of the angle.

Another drawback of the "contact angle" method is that it is applicable only to flat and smooth surfaces, otherwise the irregularities of the surface would affect the tangent angle measurement.

Yet another drawback of the "contact angle" method of the prior art is that the measurement starts from the assumption of an ideal droplet whose profile is an arc of circumference, while in the real world the profile is affected by the gravity force on the droplet liquid. FIG. 1a shows the effect of the gravity on a droplet and the corresponding angle of contact, compared to the ideal represented in FIG. 1b. To minimize the gravity influence on the droplet shape, the volume of the test droplet should be decreased to the order of $\mu l$, but this would add serious difficulties to dispensing and measuring operations.

For the above reasons a more accurate and reliable method would be highly desirable. It is an object of the present invention to provide a technique which overcomes the above drawbacks.

DISCLOSURE OF THE INVENTION

According to the present invention, we provide a method for analysing the characteristics of a surface of an article, comprising the steps of maintaining the article so that the surface faces downwards, incrementally dispensing a volume of liquid against the surface, and determining a measure indicative of the gravity force necessary to overcome the adhesion forces between the liquid and the surface.

Also according to the present invention we provide an apparatus for estimating the adhesiveness of a surface of an article, the apparatus comprising means for maintaining the article so that the surface faces downwards, means for incrementally dispensing a volume of liquid against the surface, and means for determining a measure indicative of the gravity force necessary to overcome the adhesion forces between the liquid and the surface.

BRIEF DESCRIPTION OF THE DRAWINGS

Various embodiments of the invention will now be described in detail by way of examples, with reference to accompanying figures, where.

DESCRIPTION OF THE PREFERRED EMBODIMENTS

The method according to the present invention is based on the interactions between a test liquid droplet and a solid surface to be analysed. According to a preferred embodiment of the present invention, a liquid droplet is dispensed on the solid surface under test, which is maintained upside down. The liquid will stick onto the surface if the mutual attractive forces between the liquid droplet and the solid surface are able to overcome the gravity force. An increasing volume of liquid is dispensed until the droplet reaches a critical weight for which the gravity force overcomes the adhesion forces and some of the liquid drops. The higher this critical weight, the stronger the mutual attraction between the liquid and the solid surface. According to a preferred embodiment of the present invention, the critical weight of the dispensed liquid necessary to overcome the mutual attractive forces can be used as an indication of the adhesion properties of the solid surface for a given liquid.

The critical weight described above depends on the following factors:

liquid surface tension;
liquid specific gravity;
solid surface energy;
solid-liquid interface energy;
solid surface roughness.

The first two factors can be considered constant because they depend only on the nature of the liquid; the other three factors give an indication of the adhesion properties of the solid surface. A surface adhesion scale, based on the critical weight, can be built for a given liquid in order to have an immediate representation of the adhesiveness of the surface. As mentioned above the adhesion properties of a surface can be affected by the degree of cleanliness of the surface (i.e. organic contamination on inorganic surfaces). A possible use of the method of the present invention is to determine the cleanliness of a surface, if experimental values are available. The recorded results can be compared with expected values of an ideally clean surface or even normalized into a more easily readable scale to have an immediate representation of the surface adhesion.

Figure 1:
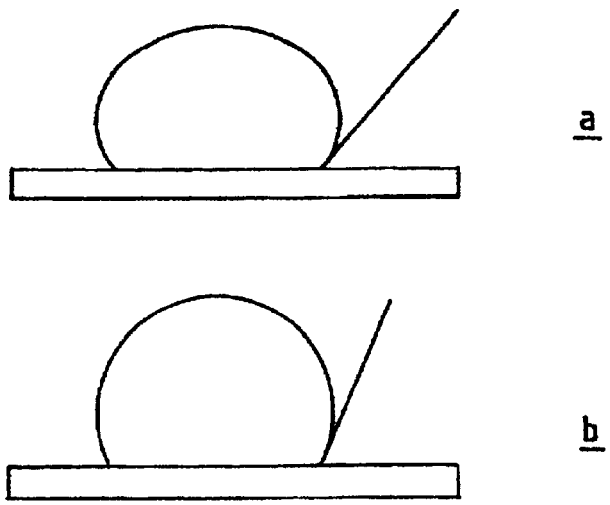
FIG. 1a shows schematically the contact angle between a liquid droplet and a surface with the deformation caused by the gravity force.
FIG. 1b shows the ideal droplet shape and angle of contact.
Figure 2:
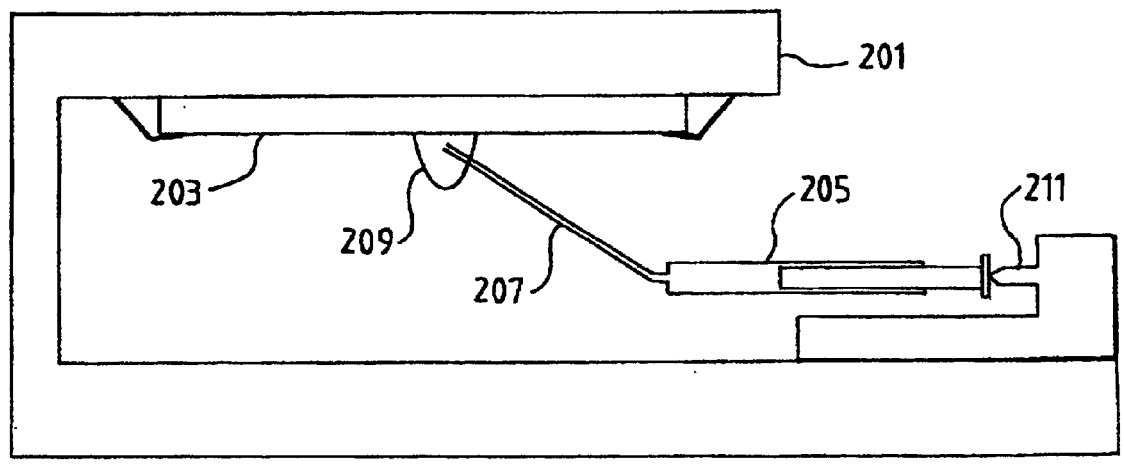
FIG. 2 shows schematically the measurement apparatus according to a preferred embodiment of the present invention.

FIG. 2 shows schematically an apparatus according to a preferred embodiment of the present invention. A solid surface 203, to be analysed, is held in place by a sample holder on a support 201. A liquid droplet 209 is dispensed by a graduated microsyringe 205 through a needle 207. According to a preferred embodiment of the present invention, the needle 207 is made of Teflon, is kept very close to the surface (about 1 mm) and its inside diameter is about 1 mm. The syringe 205 may have a motor 211, able to apply a constant pressure on the liquid to be dispensed. According to a preferred embodiment of the present invention the syringe 205 dispenses an increasing volume of liquid with a constant delivery of about 60–140 $\mu l/min$; the liquid droplet 209 will stick to the solid surface 203 until the gravity force due to its mass exceeds the mutual attractive forces between the droplet 209 and the surface 203: when this happens some of the liquid will drop. The critical weight (mass) of the liquid droplet can be easily calculated by the dispensed liquid volume, e.g. by means of a graduation on the syringe. At the moment at which the liquid starts dropping, the critical weight (or dispensed liquid volume) is measured and can be easily determined by an operator. The dispensing can be stopped. Alternatively an automatic switch may be used, e.g. an electronic sensor placed under the droplet which senses when the liquid starts dropping.

The following are some examples of analytical results obtained applying the above described method to different surfaces and using DI water as a test liquid. The results are expressed in mg and indicate the critical weight at which some of the liquid drops for the action of the gravity force; the bigger the value the stronger the adhesion forces between the surface and the liquid. Since the liquid and the test conditions are the same for all the surfaces, this experimental value is a good indicator od the adhesion properties of the tested surface:

| PET (poly-Ethiylene-Terephtalate) | 45 mg |
| Glass (ultra cleaned surface) | 290 mg |
| Alluminium (solvent cleaned surface) | 155 mg |

What is claimed is:

1. A method for analysing the characteristics of a surface of an article, said method comprising the steps of:
   maintaining the article so that the surface faces downwards;
   incrementally dispensing a volume of liquid against the surface; and
   determining a measure indicative of the gravity force necessary to overcome the adhesion forces between the liquid and the surface.

2. The method of claim 1 wherein the measure indicative of the gravity force includes the thresholds weight of the liquid at which part of the liquid drops.

3. The method of claim 1 wherein the measure indicative of the gravity force includes the volume of liquid at which a liquid droplet exceeds the thresholds weight.

4. The method of claim 1 further comprising:
   determining the adhesiveness of the surface based on the measure indicative of the gravity force.

5. A method for estimating the adhesiveness of a surface of an article comprising the steps of:
   analysing the surface according to the method of claim 1;
   comparing the measure indicative of the gravity force with a scale of experimental values.

6. A method for revealing and estimating contamination on an inorganic surface comprising the steps of:
   analysing the inorganic surface according to the method of claim 1;
   comparing the measure indicative of the gravity force with expected values for clean surfaces.

7. The method of claim 1 wherein the droplet liquid is DI water.

8. An apparatus for estimating the adhesiveness of a surface of an article, the apparatus comprising:
- a holder for maintaining the article so that the surface of the article faces downwards;
- a dispenser for incrementally dispensing a volume of liquid against the surface; and
- a measuring structure for determining a measure indicative of the gravity force necessary to overcome the adhesion forces between the liquid and the surface.

9. The apparatus of claim 8 further comprising:
- a comparator for comparing said measure with experimental values.

10. The apparatus of claim 8 wherein the measure indicative of the gravity force includes the thresholds weight at which part of the liquid drops.

11. The apparatus of claim 8, wherein the measure indicative of the gravity force includes the volume at which a liquid droplet reaches the thresholds weight.

12. The apparatus of claim 8 wherein the dispenser for dispensing the volume of liquid includes a syringe.

13. The apparatus of claim 11 wherein the measuring structure for determining the measure indicative of the gravity force includes a graduation on the syringe.

* * * * *